United States Patent [19]

Lintner et al.

[11] Patent Number: 5,102,874
[45] Date of Patent: Apr. 7, 1992

[54] ANTIMICROBIAL MIXTURES CONTAINING QUATERNARY AMMONIUM COMPOUNDS AND A QUATERNARY PHOSPHONIUM COMPOUNDS

[75] Inventors: Karl Lintner, Duesseldorf; Reinhard Orth, Monheim; Rudolf Lehmann, Leichlingen; Hans-Juergen Mueller, Duesseldorf, all of Fed. Rep. of Germany

[73] Assignee: Ecolab Inc., St. Paul, Minn.

[21] Appl. No.: 569,495

[22] Filed: Aug. 20, 1990

Related U.S. Application Data

[63] Continuation of Ser. No. 285,380, Dec. 15, 1988, abandoned, which is a continuation of Ser. No. 87,538, Aug. 20, 1987, abandoned.

[30] Foreign Application Priority Data

Aug. 25, 1986 [DE] Fed. Rep. of Germany ....... 3628801

[51] Int. Cl.⁵ ...................... A01N 57/00; A01N 57/34
[52] U.S. Cl. ...................................... 514/75; 514/129; 514/139; 514/643; 564/282; 568/9
[58] Field of Search ................. 565/282, 18; 514/643, 514/25, 129, 75, 139

[56] References Cited

U.S. PATENT DOCUMENTS

| | | | |
|---|---|---|---|
| 3,836,669 | 9/1974 | Dadekian | 514/642 |
| 3,998,754 | 12/1976 | Oswald | 252/351 |
| 4,078,087 | 3/1978 | Hyman | 514/643 |
| 4,188,380 | 2/1980 | Oswald | 514/75 |
| 4,464,398 | 8/1984 | Sheets et al. | 514/643 |
| 4,874,526 | 10/1989 | Grade et al. | 514/129 |

FOREIGN PATENT DOCUMENTS 0109354  5/1984  European Pat. Off. .

OTHER PUBLICATIONS

K. Othmer, Encyclopedia of Chem. Tech., 3rd Ed., vol. 19, 1982 p. 530.
Chemical Abstract 84:180392v, Oswald (1976)
Atlas, *Microbiology*, (1984), Macmillian, New York, pp. 746-748.

Primary Examiner—Mukund J. Shah
Assistant Examiner—Philip I. Datlow
Attorney, Agent, or Firm—Patrick J. Span; Wayne C. Jaeschke; Henry E. Millson

[57] ABSTRACT

Antimicrobial mixtures contain quaternary ammonium compounds and quaternary phosphonium compounds in a ratio by weight of from 1:9 to 9:1.

21 Claims, No Drawings

ANTIMICROBIAL MIXTURES CONTAINING QUATERNARY AMMONIUM COMPOUNDS AND A QUATERNARY PHOSPHONIUM COMPOUNDS

This application is a continuation of application Ser. No. 07/285,380 filed on Dec. 15, 1988 which is a continuation of Ser. No. 07/087,538 filed on Aug. 20, 1987 both now abandoned.

BACKGROUND OF THE INVENTION

1. Field of the Invention

This invention relates to antimicrobial mixtures containing quaternary ammonium compounds and quaternary phosphonium compounds.

2. Statement of Related Art

The use of quaternary ammonium halides as active components in antimicrobial preparations has long been known, see for example K. Lindner, Tenside-Textilhilfsmittel-Waschrohstoffe, 2nd Edition, Vol. 1, Wissenschaftliche Verlagsgesellschaft mbH, Stuttgart 1964, page 984 and Kirk Othmer, Encyclopedia of Chemical Technology, 3rd Edition, Vol. 19, John Wiley & Sons, New York, Chichester; Brisbane, Toronto, Singapore, 1982, page 530. The use of quaternary phosphonium halides as bactericides and fungicides has also been known for some time, see for example U.S. Pat. No. 3,998,754/U.S. Pat. No. 4,188,380 and Chemical Abstracts, Volume 84, Report 180 392v (1976).

In the field of disinfectants and perspectives, environmental and economic factors have given rise to a need for active components and active component combinations which show adequate antimicrobial activity, even in low in-use concentrations. Not only new compounds, but also synergistic combinations of already known active components are of interest in this connection.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that combinations of quaternary ammonium halides of the benzalkone type and certain quaternary phosphonium halides show synergistic antimicrobial activity when the two components are present in a certain ratio by weight to one another.

Accordingly, the present invention relates to antimicrobial mixtures containing a) at least one antimicrobially active quaternary ammonium compound and b) at least one antimicrobially active quaternary phosphonium compound, wherein components a) and b) are present in a ratio by weight of a:b of from 1:9 to 9:1.

Suitable antimicrobially active quaternary ammonium compounds (component a)) are, in particular, compounds of the benzalkone type which corresponding to the following formula

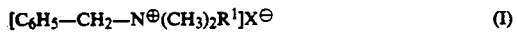     (I)

in which $R^1$ is a preferably straight-chain $C_8$–$C_{18}$ alkyl radical and $X^\ominus$ is a halide anion, preferably a chloride anion. These quaternary ammonium compounds can be present in the mixtures according to the invention either individually or in admixture with one another. Examples of antimicrobially active quaternary ammonium compounds of this type are benzyl dimethyl-n-decyl ammonium chloride, benzyl dimethyl-n-dodecyl ammonium chloride, benzyl dimethyl-n-tetradecyl ammonium chloride, benzyl dimethyl-n-octadecyl ammonium chloride and benzyl dimethyl cocosalkyl ammonium chloride, in which the radical $R^1$ from formula I is derived from the hydrogenated fatty acid mixture of coconut oil. Benzyl dimethyl-n-dodecyl ammonium chloride and benzyl dimethyl-n-tetradecyl ammonium chloride and mixtures of these compounds are preferred.

Suitable antimicrobially active quaternary phosphonium compounds (component b)) are, in particular, compounds corresponding to the following formula

     (II)

in which $R^2$ is a $C_1$–$C_6$ alkyl radical, a $C_1$–$C_6$ hydroxyalkyl radical or a phenyl radical, $R^3$ is a $C_8$–$C_{18}$ alkyl radical and $Y^\ominus$ is a halide anion, more especially a chloride anion or a bromide anion. The radicals $R^2$ and $R^3$ in formula II are preferably straight-chain radicals. The quaternary phosphonium compounds can be present in the mixtures of the invention either individually or in admixture with one another. Examples of quaternary phosphonium compounds of the above type are trimethyl-n-dodecyl phosphonium chloride, triethyl-n-decyl phosphonium bromide, tri-n-propyl-n-tetradecyl phosphonium chloride, trimethylol-n-hexadecyl phosphonium chloride, tri-n-butyl-n-decyl phosphonium chloride, tri-n-butyl-n-dodecyl phosphonium bromide, tri-n-butyl-n-tetradecyl phosphonium chloride, tri-n-butyl-n-hexadecyl phosphonium bromide, tri-n-hexyl-n-decyl phosphonium chloride, triphenyl-n-dodecyl phosphonium chloride, triphenyl-n-tetradecyl phosphonium bromide and triphenyl-n-octadecyl phosphonium chloride. Tri-n-butyl-n-tetradecyl phosphonium chloride is preferred.

For the preparation of ready-to-use antimicrobial compositions, the antimicrobial mixtures of the invention can be made up in the form of aqueous concentrates in which the total concentration of components a) and b) makes up from 30 to 50% by weight. Where the aqueous ready-to-use antimicrobial compositions are used for disinfection and preservation, the total concentration of components a) and b) is generally between 0.005 and 5% by weight, based on the composition as a whole.

In the most simple case, the ready-to-use antimicrobial mixtures consist of an aqueous solution in which the quaternary ammonium compound and the quaternary phosphonium compound are dissolved in the ratio indicated and in the concentration indicated. In most cases, the mixtures intended for practical application contain other typical constituents selected according to the particular formulation and application envisaged. In addition to water, other suitable solvents for liquid formulations are mixtures of water and water-miscible organic solvents, for example ethanol, isopropanol, ethylene glycol, propylene glycol, ethyl ethylene glycol and propyl propylene glycol. Solutions such as these may readily be sprayed using either compressed air or a propellant of the type commonly used in the aerosol field for the production of sprays.

If, in addition to its antimicrobial effect, the preparation is also required to have a detergent effect, the mixtures according to the invention may contain surfactants, particularly nonionic surfactants. Examples of suitable surfactants are adducts of from 4 to 40 moles and preferably from 4 to 20 moles ethylene oxide with 1 mole fatty alcohol, alkyl cyclohexanol, alkylphenol, fatty acid, fatty amine, fatty acid amide or alkane sulfonamide. Adducts of from 5 to 16 ethylene oxide with coconut oil or tallow fatty alcohols, with oleyl alcohol, a mixture of oleyl alcohol and cetyl alcohol and with mono-, di- or trialkylphenols and also with monoalkyl cyclohexanols containing from 6 to 14 carbon atoms in the alkyl radicals are of particular interest. Mixed adducts of ethylene oxide and propylene oxide with the above-disclosed compounds containing an active hydrogen atom are also suitable. The above alkoxylation products can also be blocked by terminal groups, for example by ether or acetal groups.

The mixtures of the invention can also contain builders. Suitable builders are, for example, alkali metal salts of gluconic acid, particularly sodium gluconate, alkali metal salts of nitrilotriacetic acid, ethylenediamine tetra-acetic acid, hydroxyethane diphosphonic acid, phosphonobutane tricarboxylic acid, lactic acid, citric acid or tartaric acid. Other suitable builders are the water-soluble salts of relatively high molecular weight polycarboxylic acids, for example polymers of maleic acid, itaconic acid, fumaric acid and citric acid. Copolymers of these acids with one another or with other polymerizable monomers, such as for example ethylene, propylene, acrylic acid, vinyl acetate, isobutylene, acrylamide and styrene, can also be used.

The mixtures of the invention can also contain detergency enhancers, such as fatty acid mono- and diethanolamides, for example coconut oil fatty acid monoethanolamide and coconut oil fatty acid diethanolamide, and adducts of up to 4 moles of ethylene oxide or propylene oxide with $C_{12}$–$C_{18}$ alkylamines of $C_8$–$C_{12}$ fatty alcohols, and free $C_8$–$C_{12}$ fatty alcohols, and also cellulose-based detergency enhancers.

In addition, it can be of advantage for other applications for the mixtures of the invention to contain other antimicrobially active substances in addition to the combination of the invention of quaternary ammonium compounds and quaternary phosphonium compounds.

In addition to liquid concentrates, solid products containing the antimicrobial mixtures of the invention can be formulated, preferably in powder or granulate form, for the production of ready-to-use detergent solutions with a disinfecting action.

The antimicrobial mixtures of the invention can be used as disinfectants and preservatives in various fields, for example in surface disinfection in hospitals, schools, swimming baths, public transport, institutions, and industrial plants. The mixtures of the invention are of particular importance for disinfection in agriculture, in dairies and breweries and other branches of the food and beverage industry. In addition, the mixtures of the invention can be used in the preservation of commercial products, such as dye dispersions, adhesives, drilling and cutting oils or products of the paper-, cardboard- or leather-processing industries, and also for the preservation of industrial water and raw water. Finally, the mixtures of the invention can also be used for the protection of materials, for example, for the impregnation of wood. In this particular case, boxes of the type used in the commercial cultivation of fungi may be effectively treated against attack by the culture mycelium.

The invention will be illustrated but not limited by the following examples.

EXAMPLES

EXAMPLE 1

The following concentrates (products C to F) according to the invention were prepared from benzyl dimethyl-n-dodecyl/n-tetradecyl ammonium chloride (70 mole % $C_{12}$; 30 mole % $C_{14}$; product A) and tri-n-butyl-n-tetradecyl phosphonium chloride (product B):

Product C (ratio a:b = 3:1)

3 parts by weight product A
1 part by weight product B
6 parts by weight water

Product D (ratio a:b = 1:9)

0.4 part by weight product A
3.6 parts by weight product B
6 parts by weight water Product E (ratio a:b = 9:1)

3.6 parts by weight product A
0.4 part by weight product B
6 parts by weight water Product F (ratio a:b = 1:3)

1 part by weight product A
3 parts by weight product B
6 parts by weight water

The microbistatic activity of the mixtures of the invention (products C to F) by comparison with that of the individual components benzyl dimethyl-n-dodecyl/n-tetradecyl ammonium chloride (product A) and tri-n-butyl-n-tetradecyl phosphonium chloride (product B) was tested against the following test microorganism suspensions:

| | | |
|---|---|---|
| 1. Escherichia coli | 2 × $10^9$ organisms/ml |
| 2. Pseudomonas aeruginosa | 5 × $10^8$ organisms/ml |
| 3. Aspergillus niger | 5 × $10^7$ organisms/ml |
| 4. Penicillium camerunense | 5 × $10^7$ organisms/ml |
| 5. Penicillium funiculosum | 3 × $10^7$ organisms/ml |
| 6. Trichoderma viride | 6 × $10^7$ organisms/ml |

The inhibiting concentrations of the products and product mixtures to be tested were determined in accordance with the guidelines for the testing and evaluation of chemical disinfection methods, chapter 2.1, printed in Zbl. Bakt. Hyg., I Abt. Orig. B 172, 536–537. The conditions described therein were modified to the extent that the following active-substance concentrations (in ppm) were tested for Pseudomonas aeruginosa and Aspergillus niger: 100, 75, 45, 30, 20, 15 and 10. For all the other test microorganisms, the active-substance concentrations (in ppm) were 50, 20, 15, 9, 6, 4, 3, and 2.

The results obtained are shown in Table I below.

TABLE I

| Inhibiting concentrations (in ppm) of products A to F | | | | | | |
|---|---|---|---|---|---|---|
| | Test Microorganism | | | | | |
| Product | 1 | 2 | 3 | 4 | 5 | 6 |
| A | 20 | 75 | 100 | 50 | 5 | 20 |
| B | 9 | 45 | 50 | 5 | 5 | 5 |
| C | 15 | 75 | 75 | 3 | 2 | 6 |
| E | 20 | 75 | 100 | 6 | 2 | 9 |
| D | 9 | 45 | 30 | 2 | 2 | 3 |
| F | 9 | 30 | 30 | 2 | 3 | 3 |

EXAMPLE 2

For impregnation, spruce wood plates measuring 10×20×2 cm were immersed for 1, 2 and 4 minutes in a treatment solution consisting of

- 2.0 parts by weight benzyl dimethyl-n-dodecyl/n-tetradecyl ammonium chloride (70 mole % n-$C_{12}$; 30 mole % n-$C_{14}$)
- 0.5 parts by weight tri-n-butyl-n-tetradecyl phosphonium chloride
- 97.5 parts by weight water and then dried. The pretreated plates were placed vertically in wooden boxes freshly filled with compost and then exposed for 12 weeks to the conditions of a mushroom culture cycle (16°-18° C.; 85.95% air humidity). Spruce wood plates which had only been impregnated with water for 30 seconds were used as control samples.

After the mushroom boxes had been emptied, the wooden plates were examined and evaluated on the following scale:

1 no mycelium traces
2 slight mycelium traces
3 isolated, very thin mycelium traces
4 slightly more than only isolated mycelium traces
5 relatively large mycelium areas, isolated unaffected areas
6 relatively large mycelium areas, but thin covering, no unaffected areas
7 entire plate affected, locally thick mycelium covering
8 entire plate affected, large areas with a relatively thick mycelium covering
9 entire plate affected by thick mycelium covering The results obtained are set out in Table II below.

TABLE II

Inhibition of the growth of mushroom mycelium on spruce wood (12 weeks; 16-18° C.; 85-95% air humidity)

| | Immersion time, min. | \multicolumn{6}{c|}{Evaluation - Test Plates} | Average |
| | | 1 | 2 | 3 | 4 | 5 | 6 | |
|---|---|---|---|---|---|---|---|---|
| Example 2 | .1 | 3 | 6 | 5 | 3 | 5 | 4 | 4.3 |
| treatment | 2 | 3 | 2 | 5 | 2 | 4 | 5 | 3.5 |
| solution | 4 | 3 | 5 | 2 | 5 | 6 | 2 | 3.8 |
| Water | 0.5 | 5 | 7 | 6 | 7 | 6 | 6 | 6.2 |

EXAMPLE 3

A stall disinfectant was prepared by mixing the following components

- 5.0 parts by weight phosphonobutane tricarboxylic acid
- 10.0 parts by weight potassium hydroxide
- 2.0 parts by weight adduct of 12 moles ethylene oxide with 1 mole $C_8$-$C_{18}$ fatty amine
- 1.5 parts by weight benzyl dimethyl-n-dodecyl/n-tetradecyl ammonium chloride (70 mole % $C_{12}$; 30 mole % $C_{14}$)
- 0.5 parts by weight tri-n-butyl-n-tetradecyl phosphonium chloride
- 81.0 parts by weight water of condensation

EXAMPLE 4

A disinfecting cleaning preparation for milking installations was prepared by mixing the following individual components:

- 15 parts by weight sodium metasilicate, anhydrous
- 40 parts by weight sodium carbonate
- 8 parts by weight tetrasodium hydroxyethane diphosphonate
- 0.5 parts by weight benzyl dimethyl-n-dodecyl/n-tetradecyl ammonium chloride (70 mole % $C_{12}$; 30 mole % $C_{14}$)
- 0.5 part by weight tri-n-butyl-n-tetradecyl phosphonium chloride
- 35 parts by weight sodium sulfate, anhydrous
- 1 part by weight silicone-based antifoam agent.

We claim:

1. An antimicrobial composition comprising an antimicrobially active component, said antimicrobial component consisting essentially of a mixture of a) at least one antimicrobially active quaternary ammonium compound of the formula

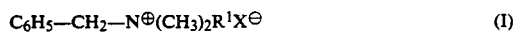

$$C_6H_5—CH_2—N^{\oplus}(CH_3)_2R^1 X^{\ominus} \qquad (I)$$

in which $R^1$ is a $C_8$-$C_{18}$ alkyl radical, and $X^{\ominus}$ is a halide anion, and b) at least one antimicrobially active quaternary phosphonium compound of the formula

$$[(R^2)_3 P^{\oplus} R^3] Y^{\ominus} \qquad (II)$$

wherein $R^2$ is a $C_1$-$C_6$ alkyl radical, a $C_1$-$C_6$ hydroxyalkyl radical, or a phenyl radical, $R^3$ is a $C_8$-$C_{18}$ alkyl radical, and $Y^{\ominus}$ is a halide anion, and wherein components a) and b) are present in a ratio by weight of a:b of from about 1:9 to about 9:1.

2. The antimicrobial composition of claim 1 wherein in component a) the $R^1$ group is a straight chain alkyl radical.

3. The antimicrobial composition of claim 1 wherein in component a) $X^{\ominus}$ is $Cl^{\ominus}$.

4. The antimicrobial composition of claim 2 wherein in component a) $X^{\ominus}$ is $Cl^{\ominus}$.

5. The antimicrobial composition of claim 1 wherein component a) is at least one of benzyl dimethyl-n-dodecyl ammonium chloride and benzyl dimethyl-n-tetradecyl ammonium chloride.

6. The antimicrobial composition of claim 1 wherein in component b) $Y^{\ominus}$ is $Cl^{\ominus}$ or $Br^{\ominus}$.

7. The antimicrobial composition of claim 1 wherein in component b) $R^2$ and $R^3$ are straight chain alkyl radicals.

8. The antimicrobial composition of claim 1 wherein component b) is tri-n-butyl-n-tetradecyl phosphonium chloride.

9. The antimicrobial composition of claim 5 wherein component b) is tri-n-butyl-n-tetradecyl phosphonium chloride.

10. An aqueous antimicrobial composition in the form of an aqueous concentrate which contains the antimicrobial composition of claim 1, wherein the total concentration of components a) and b) is from about 30 to about 50% by weight, based on the weight of the aqueous concentrate.

11. An aqueous antimicrobial composition in the form of an aqueous concentrate which contains the antimicrobial composition of claim 9, wherein the total concentration of components a) and b) is from about 30 to about 50% by weight, based on the weight of the aqueous concentrate.

12. An aqueous antimicrobial composition which contains the antimicrobial composition of claim 1, wherein the total concentration of components a) and b)

is from about 0.005 to about 5% by weight, based on the weight of the aqueous composition.

13. An aqueous antimicrobial composition which contains the antimicrobial composition of claim 9, wherein the total concentration of components a) and b) is from about 0.005 to about 5% by weight, based on the weight of the aqueous concentrate.

14. A method for the disinfection of an animal stall comprising applying to said stall the composition of claim 12.

15. A method for the disinfection of an animal stall comprising applying to said stall the composition of claim 13.

16. A method for the disinfection of a milking plant comprising applying to said plant the composition of claim 12.

17. A method for the disinfection of a milking plant comprising applying to said plant the composition of claim 13.

18. A method for the protection of wood from "microbial contamination" comprising applying thereto the composition of claim 12.

19. A method for the protection of wood from "microbial contamination" comprising applying thereto the composition of claim 13.

20. A method for disinfecting a hard surface comprising applying thereto the composition of claim 12.

21. The antimicrobial composition of claim 1 wherein components a) and b) are present in a ratio by weight of a:b of from about 1:3 to about 3:1.

* * * * *